United States Patent [19]

Krall

[11] Patent Number: 4,713,235
[45] Date of Patent: Dec. 15, 1987

[54] RADIOPAQUE CYANOACRYLATES

[75] Inventor: Robert E. Krall, Raleigh, N.C.

[73] Assignee: CRX Medical, Inc., Raleigh, N.C.

[21] Appl. No.: 450,249

[22] Filed: Dec. 16, 1982

Related U.S. Application Data

[63] Continuation-in-part of Ser. No. 267,400, May 26, 1981, abandoned, which is a continuation-in-part of Ser. No. 198,466, Oct. 20, 1980, abandoned.

[51] Int. Cl.$^4$ ............................................. A61K 49/04
[52] U.S. Cl. .......................................... 424/5; 424/81; 424/150
[58] Field of Search ................................. 424/81, 5

[56] References Cited

U.S. PATENT DOCUMENTS

| | | | |
|---|---|---|---|
| 3,360,124 | 12/1967 | Stonehill | 206/84 |
| 4,086,266 | 4/1978 | Corey | 260/465.4 |
| 4,354,454 | 11/1982 | Hoffman | 424/5 |

OTHER PUBLICATIONS

Cromwell et al., AJR:132, May, 1979, pp. 799–801.
Neuwirth et al., (I), Am. J. Obstet. Gynecol., 10-1-77, pp. 348–349.
Neuwirth et al., (II), Am. J. Obstet. Gynecol., 4-1980, pp. 951–956.
Physicians Desk Reference for Radiology & Nuclear Medicine (PDR), 1978/79, pp. 74–85.

*Primary Examiner*—Leonard Schenkman
*Attorney, Agent, or Firm*—Vidas & Arrett

[57] ABSTRACT

Mixtures of cyanoacrylate monomers and radiopaque additives stable to the monomer produce radiopaque compositions useful in surgical and other applications. The additives useful in the compositions are triiodophenol, tetraiodethylene, iodoform and mixtures thereof. When Iodoform is included in the compositions, at least an equal molar amount of triiodophenol should also be included. The compositions include between 0.5 and 11 mole percent iodine and preferably contain at least 4 mole percent iodine. Inhibitors such as $SO_2$ and hydroquinone may also be included. The compositions are preferably compounded with cyanoacrylate monomers of greater than 98-percent purity.

15 Claims, No Drawings

RADIOPAQUE CYANOACRYLATES

This application is a continuation-in-part application of co-pending application Ser. No. 267,400, filed May 26, 1981 now abandoned as a continuation-in-part of application Ser. No. 198,466, filed Oct. 20, 1980, now abandoned.

BACKGROUND OF THE INVENTION

Methyl cyanoacrylate (MCA) and other cyanoacrylates are well known chemical products which have found wide use as adhesives for both general and medical purposes. The ability of the alkyl 2-cyanoacrylates to polymerize rapidly at room temperature in the absence of a solvent or added catalyst has resulted in the use of this class of monomers for surgical application. 2-cyanoacrylate monomers have been used as physiological adhesives in bronchial closure, the anastomosis of small arteries, intestinal anastomosis and cutaneous lacerations. Methyl cyanoacrylate has also found application in the field of permanent sterilization of mammalian females including human females. Sterilization of the female is accomplished by introduction of small quantities of MCA into the fallopian tubes where contact with body moisture polymerizes the MCA and blocks the fallopian tube. With passage of time, fibrous tissue growth replaces the MCA and permanent sterilization results. This latter use and procedure is described in U.S. Pat. Nos. 3,822,702 and 3,948,259.

For some of the medical applications of the cyanoacrylates, it is desirable that there be some means for inspecting the result of the surgical operation without the need for surgically reopening the patient. For instance, in the anastomosis of arteries or intestines, it is desirable to have some means for non-intrusively inspecting the joined tubes in order to verify that a proper weld has taken place without blockage of the tube. Conversely, where MCA is used to sterilize females, it is desirable to inspect the polymer plug to insure that tube blockage has been successfully accomplished.

Radiopaque cyanoacrylate compositions are also useful for the general adhesive applications to which cyanoacrylates are put, such as the bonding of metal, plastic or ceramic parts. Radiopacity of such compositions allows inspection of the integrity of the joined seam. For instance, in the manufacture of electronic microchips it has been suggested that MCA may be a useful adhesive for joining contact leads to the chips. Since a major failure mode of electronic chips occurs at the chip-lead interface, it would be advantageous if such cyanoacrylate adhesives were radiopaque so that the weld could be examined.

If the cyanoacrylate ester is made radiopaque, the desired inspection may be accomplished by x-ray of the affected area. However, the polymerization properties which make cyanoacrylate esters useful in medical and other applications have heretofore prevented formulation of radiopaque compositions. The highly unstable cyanoacrylate esters polymerize under many conditions, including exposure to even trace amounts of moisture, oxygen, heat, high energy radiation and active organic sites to note a few. As a result, many of the known radiopaque materials commonly used in other applications cannot be incorporated into the monomer as a radiopaque additive for cyanoacrylate esters. Most radiopaque materials reduce the stability of the esters and, in some cases, even initiate polymerization thereof.

In particular, it has been found that organic iodo compounds commercially available as x-ray screening agents are frequently available as sodium salts of a carboxylic acid or as compounds containing primary or secondary amino groups. These materials are not stable to cyanoacrylates and cause polymerization thereof.

BRIEF DESCRIPTION OF THE INVENTION

As originally contemplated, an aspect of the present invention involved the preferred use of organic iodo acids, particularly iodo carboxylic acids, as radiopaque agents because carboxylic acids are known anionic inhibitors. Thus, compositions in which the radiopaque additives actually stabilize the monomer rather than destabilizing it were expected. Another aspect of the invention, as originally contemplated, involved the use of additive materials in suspension, rather than in solution in the cyanoacrylate monomer. The use of suspensions is necessitated by the solubility limits on most radiopaque materials, and particularly the iodo carboxylic acids, which are at or below the minimum useful concentrations of iodine for most applications.

Iodo acids can serve a dual role as both an anionic inhibitor in radiopaque agents. However, significant problems relating to the low solubility of the additives have arisen which severely limit the usefulness of the majority of compositions originally contemplated as being within the scope of the present invention.

The cyanoacrylate esters are very thin, nonviscous liquids which typically means that very narrow orifice applicators must be used. If suspensions of large particles relative to the applicator orifice is used, the orifices can easiy become plugged. Complete and permanent occlusion of a narrow orifice by polymerized monomer commonly follows. Compositions useful in the general applications contemplated for the present invention have a minimum concentration of about 0.5 mole percent iodine atoms (calculated as iodine atoms per molecules of composition constituents), with a minimum of about 3 to 4 mole percent for most applications, including all medical applications. With concentrations as low as 0.5 mole percent, only very shallow applications of the cyanoacrylates-radiopaque compositions are usable. That is, deep body use is inoperative to show the composition by X-ray, while shallow body usage, such as on a head, is operable to show the material by X-ray. Since most of the iodo carboxylic acids have been found to have a solubility of less than about 0.2 mole percent (equivalent to about 0.6 mole percent iodine atoms for tri-iodo compounds), iodo carboxylic acid compositions require a substantial amounts of suspended material to achieve the requisite iodine concentrations for all but the least critical general applications. While finely divided additive materials can be shaken to produce transient suspension compositions, the large amount of undissolved additives needed for most such compositions results in the growth of relatively large cystals of undissolved additive over a period of a few hours or days. Such crystals are not easily evenly resuspended in the non-viscous ester or delivered through conventional applicator orifices.

It is an object of the present invention to produce stable cyanoacrylate compositions which include radiopaque additives, the compositions containing between about 0.5 and 11 mole percent iodine or even higher and the additives being sufficiently soluble that they remain in solution or return to solution with only short term heating at mild temperatures.

It is a further object of the present invention to describe novel X-ray contrast media. Such novel contrast media comprise a radiopaque agent selected from the group consisting of triiodophenol and iodoform.

Still further objects of the present invention are novel methods for sterilization of mammalian females using radiopaque cyanoacrylate compositions and for preparation of such radiopaque compositions.

The inventive combinations are mixtures of cyanoacrylate esters with triiodophenol alone, or in combination with iodoform, tetraiodoethylene or both. When iodoform is included in the compositions, triiodophenol is maintained in an equal or greater molar amount. Polymerization inhibitors, such as hydroquinone or hydroquinone monomethylethyl ether, are also preferably included in the inventive compositions.

DETAILED DESCRIPTION OF THE INVENTION

The radiopacity of the compositions of the present invention is directly related to the number of iodine atoms included in the composition. As used herein, this number is expressed as mole percent iodine and is calculated as the pecentage ratio of total iodine atoms in the composition to the total number of molecules in the composition (cyanoacrylate monomer plus radiopaque and inhibitor additives). Mole percent and parts per million (ppm) numbers given for additive molecules are likewise calculated as fractions of the total number of molecules in the composition. In the examples which follow, methyl cyanoacrylate was used. The source was Eastman under their designation MCA 910, a 98% pure methyl cyanoacrylate.

For most general and medical applications the cyanoacrylate compositions of the present invention typically should contain at least 4 mole percent iodine. Substantially higher concentrations for certain types of applications may be necessary. For instance, for fallopian tube blockage, concentrations of 7–10 mole percent, or even higher are desirable because of the very small diameter of the fallopian tubes and the relatively high background opacity of the abdominal region. For some industrial applications much less background radiopacity is present and therefore lower amounts of the iodine-containing additives may be used.

As previously stated, the iodine-containing additives in the compositions of the present invention are triiodophenol, iodoform and tetraiodoethylene. Each of these three iodine-containing additives are solids at ambient temperatures with limited solubility in MCA. The maximum solubility at ambient temperatures with triiodophenol (2, 4, 6-triiodophenol) is approximately 1.5 mole percent. The limits for iodoform alone is approximately 1.1 percent and for tetraiodoethylene alone, approximately 0.3 percent. Both triiodophenol and tetraiodoethylene, however, are believed to form charge transfer complexes with iodoform in cyanoacrylate solution. As a consequence, solubilities of each are significantly increased when included in combination. Solutions as high as about 11 mole percent iodine may be achieved by including all three additives in optimum ratios. In combination, triiodophenol may be included up to a maximum of about 2 mole percent, iodoform to a maximum of between about 1.5 and 1.8 mole percent and tetraiodoethylene up to about 0.4–0.5 percent.

When the inventive compositions are formulated to an iodine concentration of about 10 mole percent or greater, the resulting solutions are apparently super saturated as crystalline material will eventually precipitate. However, such precipitation is very gradual, typically taking up to 16 hours. Furthermore, the precipitated material may be easily redissolved, e.g. by heating an ampule container (hermetically sealed to moisture) of the composition for 5–15 minutes or by placing the ampule in boiling water for a few minutes. It is not known whether the precipitate is a charge transfer complex or one or more of the individual additive components.

The use of iodoform in the compositions of the present inventive has some limitations. Iodoform has a tendency to lose iodine and form the very highly reactive hydroiodocarbene upon exposure to light. Consequently, cyanoacrylate formulations including only iodoform will eventually polymerize. The combination of iodoform with at least an equal molar amount of triiodophenol substantially reduces the tendency of the iodoform to decompose to carbene. This is further evidence of a charge transfer complex. A similar but not as pronounced effect on shelf life has been noted with combinations of iodoform and tetraiodoethylene.

The stability of the compositions is also effected by the purity of the cyanoacrylate monomer. The cyanoacrylate monomer should be at least 98 percent pure before formulation. It can be generally stated that the purer the starting cyanoacrylate monomer is, the more stable the formulation made from it.

In addition to monomer and radiopaque agent compositions of the present invention will typically include additional polymerization inhibitors. Sulfur dioxide in the range of about 250–500 ppm may be added before or after final purification of the monomer. If about 500 ppm $SO_2$ is added before final purification, the purification step is believed to reduce the $SO_2$ concentration down to about 100 ppm or less.

Hydroquinone or hydroquinone monoethyl ether will typically be added together with the radiopaque additives in the formulation of the final composition. The concentrations of these inhibitors should be greater than 100 ppm, preferably between 500 and 1,000 ppm.

At the maximum concentrations of radiopaque additives, e.g., about 10–11 mole percent iodine the adhesive properties of the present compositions are somewhat diminished. However, the sclerotic properties of the compositions are retained and thus such compositions are particularly useful in female sterilization applications.

EXAMPLE I

A mixture of sterile redistilled MCA (methyl cyanoacrylate) is prepared containing 1.17 mole percent of iodoform and 1.17 mole percent 2, 4, 6-triiodophenol. 250–500 ppm $SO_2$ is added as a stabilizer during a distilization and sterilization step to insure at least 98% pure MCA monomer. About 250 ppm hydroquinone is also added. The mixture is heated with stirring to 80° C. for an hour in the dark (a low-intensity, dark room red light may be used). The resulting composition, containing 7 mole percent iodine atoms may be stored for extended periods in aluminum foil or other containers which are opaque to visible and ultraviolet light. Upon exposure to light, e.g., just prior to use, the composition is stable for two to three hours. When used as a female sterilizing agent, the polymer plug formed by this composition in the fallopian tubes is distinguishable over the pelvic background in an X-ray image. Stored at ambient temperatures in an opaque container compositions according to this formulation have retained their ability to close fallopian tubes for 5-6 months.

EXAMPLE II

A composition containing about 10.2 mole percent iodine as prepared as in Example I using MCA, 2.0 mole percent (20,000 ppm) triiodophenol, 1.0 mole percent (10,000 ppm) iodoform, 0.3 mole percent (3,000 ppm) triiodoethylene and 500 ppm hydroquinone.

EXAMPLE III

A 10.2 mole percent iodine composition is formulated as in Example II but using 1800 ppm triiodophenol and 1200 ppm iodoform together with 3000 ppm tetraiodoethylene and 500 ppm hydroquinone.

EXAMPLE IV

A composition as formulated as in Examples II and III but with the triiodophenol concentration of 1600 ppm and the iodoform concentration of 1400 ppm.

EXAMPLE V

A composition as formulated in the three previous examples but with the triiodophenol concentration being 1500 ppm and the iodoform concentration being 1500 ppm.

The projected lifetimes of the compositions of Examples II-V when MCA having a purity in excess of 98% is used is on the order of two years.

In addition to methylcyanoacrylate, other cyanoacrylate esters at least through the butyl cyanoacrylates may be used with similar results. Likewise, mixtures of cyanoacrylate monomers may also be used.

In compounding the compositions of the present invention, mild heating may be required at least for compositions in the upper ranges of iodine concentration, e.g., 7-11 mole percent, in order to effect complete dissolution of the additives. The compositions should not be heated above the boiling temperature of water (about 100° C.) and should preferably be maintained at temperatures no greater than 80° C. The heating should also be conducted in the dark to minimize the possibility of polymerization of the monomer during the compounding step. Heating should be for the minimum time required to solubilize, after which, the composition is reduced to room temperature.

In the sterilization of mammalian females a MCA composition containing between 7-11 mole percent iodine is introduced into the fallopian tubes by procedures such as those described in U.S. Pat. Nos. 3,875,939; 3,871,034; 3,822,702 or 4,119,098. The composition is permitted to spontaneously polymerize within the fallopian tubes and then the abdominal region is examined by X-ray to assure that a polymer occluding plug has formed in each tube. if the examination reveals the tubes have not both been completely occluded, the previous steps are repeated. Compositions of the foregoing Examples I-V are preferred for female sterilization applications.

What is claimed is:

1. A radiopaque polymerization cyanoacrylate composition comprising a mixture of an ester of 2-cyanoacrylic acid and a radiopaque additive stable to and not substantially decreasing the storage life of the cyanoacrylate ester, the additive including at least one member selected from the group consisting of triiodophenol, iodoform and tetraiodoethylene and the composition having between 0.5 and 11 mole percent iodine atoms.

2. A composition as in claim 1 wherein the iodine atom concentration is greater than 4 mole percent.

3. A composition as in claim 1 wherein the additive includes iodoform.

4. A composition as in claim 3 wherein the iodine atom concentration is between 7 and 11 mole percent iodine.

5. A composition as in claim 1 wherein the cyanoacrylate ester is selected from the group consisting of methyl, ethyl, propyl, isopropyl, n-butyl, sec-butyl and isobutyl cyanoacrylates and mixtures thereof.

6. A compositions as in claim 5 wherein the cyanoacrylate is at least 98% pure monomer prior to compounding.

7. A composition as in claim 5 wherein the cyanoacrylate ester is methylcyanoacrylate.

8. A composition as in claim 1 wherein the composition is a solution at ambient temperatures.

9. A composition as in claim 1 wherein the radiopaque additive includes a mixture of triiodophenol and iodoform and the triiodophenol is present in a molar amount at least equal to that of the iodoform.

10. A composition as in claim 9 wherein the triiodophenol is present in a range of between 1.17 and 2.0 mole percent, the iodoform is present in a range between 1.0 and 1.5 mole percent and wherein the composition further contains between 0 and 0.3 mole percent tetraiodoethylene.

11. A composition as in claim 10 further comprising between 100 and 750 ppm $SO_2$ and between 100 and 1,000 ppm of an antioxidant selected from the group consisting of hydroquinone and hydroquinone monomethyl-ether.

12. The composition as in claim 1 further comprising between 100 and 500 ppm $SO_2$.

13. A composition as in claim 1 further comprising between 100 and 1,000 ppm of an antioxidant selected from the group consisting of hydroquinone and hydroquinone monomethylether.

14. A method of sterilizing a mammalian female comprising:
introducing a cyanoacrylate composition into the fallopian tubes of the female, the composition comprising a mixture of methylcyanoacrylate, triiodophenol and iodoform, the mixtrue having between 7 and 11 mole percent iodoine atoms;
permitting the composition to polymerize within the fallopian tubes;
subjecting the region of the fallopian tubes to X-ray imaging to determine the extent of formation of tube-occluding polymer plugs within the fallopian tubes; and
repeating the foregoing steps until the X-ray imaging reveals that the tubes have not been completely occluded.

15. A method as in claim 14 wherein the cyanoacrylate composition further comprises tetraiodoethylene.

* * * * *